United States Patent [19]

Venturello et al.

[11] 4,226,778
[45] Oct. 7, 1980

[54] PROCESS FOR THE MANUFACTURE OF ALKYLENE CARBONATES

[75] Inventors: Carlo Venturello, Turin; Rino D'Aloisio, Novara, both of Italy

[73] Assignee: Montedison S.p.A., Milan, Italy

[21] Appl. No.: 29,564

[22] Filed: Apr. 12, 1979

[30] Foreign Application Priority Data

Apr. 14, 1978 [IT] Italy ................. 22323 A/78

[51] Int. Cl.$^2$ .................. C07D 317/36; C07D 317/38
[52] U.S. Cl. ................................. 260/340.2
[58] Field of Search ....................... 260/340.2

[56] References Cited
U.S. PATENT DOCUMENTS

| | | | |
|---|---|---|---|
| 1,907,891 | 5/1933 | Steimmig et al. | 260/340.2 |
| 2,766,258 | 10/1956 | Malkemus | 260/340.2 |
| 2,873,282 | 2/1959 | McClellan | 260/340.2 |
| 3,025,305 | 3/1962 | Verdol | 260/340.2 |
| 3,535,342 | 10/1970 | Emmons | 260/340.2 |
| 3,923,842 | 12/1975 | Wu | 260/340.2 |

Primary Examiner—Norma I. Milestone

Attorney, Agent, or Firm—Stevens, Davis, Miller & Mosher

[57] ABSTRACT

A new process is disclosed for the synthesis of alkylene carbonates having from 2 to 4 carbon atoms in the chain, starting from a corresponding halohydrin having the formula:

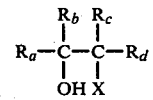

wherein $R_a$, $R_b$, $R_c$ and $R_d$ are independently hydrogen or alkyl, aryl, alkylaryl or arylalkyl radicals and where X is a halogen, characterized in that said halohydrin is reacted with a bicarbonate of a quaternary -onium compound, where "-onium" means ammonium, phosphonium, arsonium or stibonium, preferably using an organic solvent as diluent and operating in the presence of carbon dioxide.

22 Claims, No Drawings

PROCESS FOR THE MANUFACTURE OF ALKYLENE CARBONATES

THE SCOPE AND UTILITY OF THE INVENTION

This invention relates to a process for the manufacture of alkylene carbonates and particularly of alkylene carbonates having from 2 to 4 carbon atoms in the alkylene chain. Such alkylene carbonates, and in particular ethylene carbonate and propylene carbonate, have great utility for instance as solvents of organic polymers, as electrochemical solvents, and as synthesis intermediates.

BACKGROUND OF THE INVENTION

Processes for manufacturing alkylene carbonates are already well known. One such method involves the reaction of an epoxide with carbon dioxide in the presence of proper catalysts. Another method is bases on the reaction between vicinal glycols and phosgene. Still another method is based on the reaction between vicinal halohydrins and sodium bicarbonate in the presence of carbon dioxide.

Such metods as these, however, have the drawback of involving, respectively, rather high working temperatures and pressures, or the use of toxic reagents (phosgene), or of giving rise to the collateral formation of undesired by-products that are difficult to separate (glycols).

From U.S. Pat. No. 3,923,842 it is also known how to prepare alkylene carbonates by reacting vicinal halohydrins with carbon dioxide, in a solvent and in the presence of amines, according to the reaction scheme:

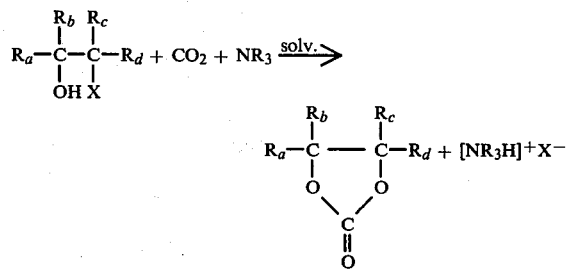

wherein R, $R_a$, $R_b$, $R_c$ and $R_d$, like or unlike one another, are hydrogen, or alkyl, aryl, alkylaryl or arylalkyl radicals, and where X is a halogen. This process, although offering considerable advantages in respect of the above-cited methods, does not seem fully satisfactory, inasmuch as the reaction develops rather slowly even at high temperatures (70°–100° C.) and requires the use of high carbon dioxide pressures to obtain appreciable results from an industrial viewpoint.

OBJECT OF THE INVENTION

Thus it is an object of the present invention to provide a method for synthesizing alkylene carbonates substantially more quickly in comparison to the methods of the art, and which permits one to operate at room temperatures and pressures with excellent yields in very short times. Still further objects and advantages will appear from the following description.

DETAILS OF THE INVENTION

In its broadest aspect, the invention relates to a process for the manufacture of alkylene carbonates, and particularly alkylene carbonates having from 2 to 4 carbon atoms in the alkylene chain, starting from a corresponding vicinal halohydrin, such process being characterized in that the halohydrin is reacted with the bicarbonate of a quaternary -onium compound, where "-onium" means ammonium, phosphonium, arsonium or stibonium, preferably in the presence of an organic diluent and of carbon dioxide.

More particularly, high yields may be obtained without any appreciable formation of glycols, in very short times, and at room temperatures and pressures, by using bicarbonates of quaternary ammonium cations, such as, for example, tetramethylammonium bicarbonate, tetraethyl-ammonium bicarbonate, terta-n-butyl ammonium bicarbonate, benzyl-trimethyl-ammonium bicarbonate. Similar results have been achieved by using strongly basic anionic resins having quaternary ammonium terminations or end groups (in the form of hydroxyls), carbonated with $CO_2$ before the synthesis. Examples of the latter are the products commercially known as KASTEL A 300, KASTEL A 300 P, KASTEL A 500, KASTEL A 500 P, AMBERLITE IRA-400-OH, KASTEL A 501 D, KASTEL A 510, and the like. Weakly basic resins having a ternary termination ($-NR_2$), such as KASTEL A 101 as per Examples 9 and 10 below, lead to results less satisfactory by far.

The termination or end groups of strongly basic resins of the quaternary type which are to be used according to this invention may be, for instance, of the type $[-N(CH_3)_3]^+$ or of the type

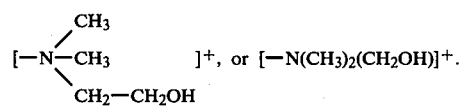

The term "halohydrins" means in particular chlorohydrins, bromohydrins and iodohydrins. As examples are the following halohydrins: ethylene chlorohydrin, ethylene bromohydrin, ethylene iodohydrin, 2-chloropropanol-1, 1-chloro-propanol-2, 2-bromopropanol-1, 1-bromo-propanol-2, 2-iodo-propanol-1, 1-iodopropanol-2, 2-chloro-butanol-1, 2-bromo-butanol-1, 2-iodo-butanol-1, erythro-3-bromo-butanol-2, threo-3-bromo-butanol-2, and mixtures thereof.

Various solvents may be employed for the synthesis according to this invention, such as for example methanol, n-butanol, acetone, dioxane, acetonitrile, dimethylformamide, benzene, toluene, xylols, dimethylsulphoxide, and the like. In tests carried out by the present inventors acetonitrile has been used with excellent results.

When bicarbonates of resins are used as carbonating agents for the halohydrins, aqueous-organic mixtures, such as water-dioxane, water-acetonitrile, and the like, may be employed as well as a solvent. In some particular cases, even water alone may be used.

The amount of ammonium compound, expressed as $NR_4^+$ groups, must be equivalent to or slightly in excess—in molar terms—in respect of the amount of halohydrin employed.

At the conclusion of the reaction, the ammonium compound is present in the form of halide, according to the reaction scheme:

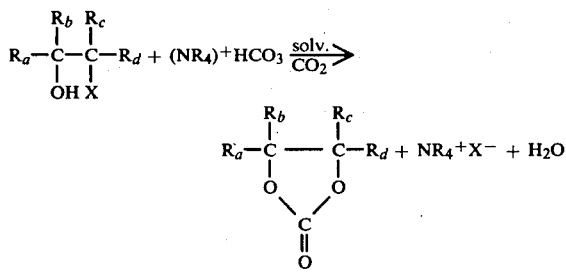

wherein the symbols have the meanings specified above.

The tetralkylammonium halide or the resin halide may be easily separated from the reaction mixture by filtration and recovered nearly quantitatively. The filtrate can be fractionated to give the required alkylene carbonate.

As an alternative, when use is made of an anion exchange resin, after conclusion of the reaction the resin is regenerated "in situ", wherefore it may be advisable to work with two or more reactors in parallel, preferably of the suspended bed type, running alternately. While one reactor works, the other is shut down and the resin is regenerated, for instance by means of dilute aqueous NaOH or $NH_4OH$ solutions and successive carbonation with $CO_2$.

The synthesis temperature may vary over a wide range. Although excellent results are obtained at room temperature or even as low as 0° C., a temperature increase may be useful, in some cases, for substantially reducing the reaction period. Of course, the reaction temperature must not exceed either the boiling point of the solvent or the degradation point of the exchange resin.

The influence exerted by the carbon dioxide pressure is not critical. Nevertheless, when operating at higher temperatures than room temperature, an increase of the $CO_2$ pressure is particularly advantageous. In principle, it is useful to operate between room pressure and 10,000 Kilopascal (Kpa) also 100 kg/cm² gauge, and preferably between room pressure and 3,000 Kpa, also 30 Kg/cm² gauge.

The following examples are given for the purpose of still better illustrating the present invention, but without being a limitation thereon.

EXAMPLE 1

46 g of a methanol solution at 24% by weight of tetramethylammonium hydroxide (about 0.12 moles) were diluted with 50 cm³ of methanol and the dilute solution was carbonated with carbon dioxide for 40 minutes. Methanol was then distilled under a slight vacuum and the residue was diluted again with 250 cm³ of acetonitrile and kept in a carbon dioxide atmosphere for about 10 minutes, until gas absorption was no longer noticed.

The remaining suspension of tetramethyl-ammonium bicarbonate in acetonitrile was additioned with 0.1 mole of ethylene bromohydrin, and the suspension at 20° C. was kept under stirring and in a $CO_2$ atmosphere for about 10 minutes. The tetramethyl-ammonium bromide so obtained was separated by filtration at 20° C. together with small amounts of tetramethyl-ammonium bicarbonate, corresponding to the excess of ammonium reagent. The filter cake was washed twice with 40 cm³ of acetonitrile each time, the washing liquid was added to the filtrate, and the whole was distilled under a slight vacuum to recover the solvent. The residual liquid was additioned with acetone and the last traces of salt which precipitated were separated by filtration. Acetone was then evaporated, so obtaining 9.63 g of an oil that solidified at room temperature.

8.45 g of solid ethylene carbonate were obtained by distillation under vacuum (73°–75° C./0.4–0.5 mm Hg). The yield was about 96% referred to the bromohydrin.

EXAMPLE 2

0.1 mole of 98% propylene iodohydrin as added to a suspension of tetramethyl-ammonium bicarbonate in acetonitrile, prepared according to Example 1, and the suspension at 20° C. was stirred in a $CO_2$ atmosphere for about 10 minutes. Tetramethyl-ammonium iodide was separated by filtration at 20° C. together with small amounts of tetramethyl-ammonium bicarbonate.

The filter cake was washed with 50 cm³ of acetonitrile, the washing acetonitrile was added to the filtered solution, and the whole was distilled under vacuum to recover the solvent. The residual liquid was diluted with acetone and 1.5 g of salt still contained therein were separated by filtration. Acetone was evaporated and the oil contained therein was distilled under vacuum (10.1 g).

9.40 g of propylene carbonate at 98.6% (gas-liquid chromatographic analysis) were obtained by distillation (59°–60° C./0.5 mm Hg). This corresponded to a yield of about 91% referred to the iodohydrin.

EXAMPLE 3

An acetonitrile suspension of tetramethyl-ammonium bicarbonate, prepared as described in Example 1, was additioned with 0.1 mole of erythro-3-bromo-butanol-2, whereupon the procedure was as specified above. The reaction time was 20 minutes. By operating according to Example 1, 11.14 g of oil were obtained, which solidified at room temperature.

By distillation under vacuum (58° C./0.05 mm Hg) 10.8 g of trans-1,2-dimethyl-ethylene carbonate were obtained. The yield was about 93%.

EXAMPLE 4

Example 3 was repeated, using threo-3-bromo-butanol-2 as reagent. The reaction time was 60 minutes.

By distillation under vacuum (70°–74° C./0.1 mm Hg), 11.3 g of cis-1,2-dimethylethylene carbonate at 97.85% were obtained. The yield was about 95.3%.

EXAMPLE 5

Example 3 was repeated, using 2-bromo-1-phenyl-ethanol as reagent and adjusting the reaction time to around 15 minutes. 16.57 g of a yellowish residual oil were obtained, which solidified at room temperature.

By distillation under vacuum (115° C./0.1 mm Hg) 15.35 g of phenylethylene carbonate were obtained, which promptly solidified. The yield was about 93.6%.

EXAMPLE 6

Example 3 was repeated, but using butylene bormohydrin as reagent and adjusting the reaction time to about 15 minutes. 12.6 g of residual oil were obtained, which, after distillation under vacuum (68°–70° C./0.4–0.5 mm Hg), provided 11.2 g of butylene carbonate (at 99% purity) in the form of a colorless oil, with a yield of about 96.4%.

EXAMPLE 7

Example 2 was repeated, using benzyl-trimethylammonium bicarbonate as ammonium reagent.

8.59 g of propylene carbonate of 98.5% purity were obtained. The yield was about 85.48%.

EXAMPLE 8

43 g of a wet, strongly basic anion exchange resin in the hydroxyl form (AMBERLITE IRA—400—OH) were suspended in 100 cm$^3$ of methanol and carbonated with $CO_2$ over about 30 minutes. The carbonated resin was filtered, washed with acetonitrile to remove the residual methanol, and suspended in 100 cm$^3$ of acetonitrile. The suspension was then kept for 10 minutes under stirring in a carbon dioxide atmosphere. The suspension was then additioned with 0.05 moles of propylene iodohydrin, whereupon the suspension was maintained under stirring for 2 hours at room temperature and in a carbon dioxide atmosphere. Finally it was filtered and the resin was washed with acetonitrile.

From the filtrate were obtained 4.7 g of propylene carbonate (gas-liquid chromatographic analysis), corresponding to a yield of 92%, and 0.46 g of unconverted iodohydrin.

EXAMPLE 9 (COMPARATIVE EXAMPLE)

Example 8 was repeated contacting 0.01 mole of propylene iodohydrin with 7.5 g of a weakly basic anion exchange resin, commercially known as KASTEL A-101, suspended in 16 cm$^3$ of a mixture containing water and dioxane in equal parts. The suspension was maintained under stirring for 4 hours at room temperature and in a carbon dioxide atmosphere, thereby obtaining 0.41 g of propylene carbonate (gas-liquid chromatographic analysis), corresponding to a yield of 40%.

EXAMPLE 10 (COMPARATIVE EXAMPLE)

Example 9 was repeated contacting, in an autoclave and under stirring, 0.04 moles of propylene iodohydrin with 30 g of a weakly basic resin (KASTEL A-101), suspended in 64 cm$^3$ of a mixture containing water and dioxane in equal parts.

The whole was heated to 60° C. and under a pressure of 3000 Kpa of carbon dioxide for 4 hours, thereby obtaining 3 g of propylene carbonate (gas-liquid chromatographic analysis), corresponding to a yield of about 73.5%.

The results of Examples 2, 7, 8, 9 and 10 are recorded in the following Table I for comparative purposes.

1.13 g of butylene carbonate were thus obtained. The yield was about 97% (gas-liquid chromatographic analysis).

EXAMPLE 12

43 g of a wet, strongly basic anion exchange resin in the hydroxyl form (AMBERLITE IRA-400-OH) were charged into an oscillating autoclave, together with 100 cm$^3$ of methanol, and carbonated at room temperature under $CO_2$ pressure (3000 Kpa or 30 Kg/cm$^2$ gauge) for 30 minutes. The autoclave was opened, the carbonated resin was filtered, washed with acetonitrile, and suspended again in the autoclave with 100 cm$^3$ of acetonitrile. The resin was kept for a further 10 minutes under $CO_2$ pressure (3000 Kpa or 30 Kg/cm$^2$ gauge), then it was degasified, vacuum was created in the autoclave, and 0.05 moles of propylene chlorohydrin were introduced thereinto by suction. $CO_2$ was charged to a pressure of 2000 Kpa or 20 Kg/cm$^2$ gauge and it was heated to 60° C. The $CO_2$ pressure increased to 3000 Kpa or 30 Kg/cm$^2$ gauge. The mixture was kept under these conditions for 1 hour. The autoclave was cooled, degasified and the resin filtered and washed with acetonitrile.

From the filtrate were obtained 4.12 g of propylene carbonate, corresponding to a yield of 80%, and about 1 g of unconverted chlorohydrin (gas-liquid chromatographic analysis).

EXAMPLE 13

Example 12 was repeated using propylene iodohydrin. The mixture was maintained at 60° C. for 30 minutes under $CO_2$ pressure (3000 Kpa or 30 Kg/cm$^2$ gauge). The conversion of the iodohydrin to propylene carbonate was practically complete.

EXAMPLE 14

Example 12 was repeated using, as a strongly basic resin, KASTEL A-300 in the hydroxylated form.

The resin in question was a resin having quaternary terminations of the type

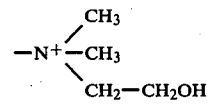

on a matrix obtained by copolymerizing styrene and divinylbenzene.

3.56 g of propylene carbonate, corresponding to a yield of about 70%, and 0.988 g of the unconverted chlorohydrin were thus obtained (gas-liquid chromatographic analysis).

TABLE I

| EXAMPLE | SOLVENT | TEMPERATURE | PRESSURE | TIME | ONIUM CATION | YIELD |
|---|---|---|---|---|---|---|
| 2 | Acetonitrile | Room | Room | 10' | Tetramethylammonium | 91.0% (*) |
| 7 | Acetonitrile | Room | Room | 10' | Benzyl-trimethylammonium | 85.5% |
| 8 | Acetonitrile | Room | Room | 2 h | Strongly basic resin | 92.0% (*) |
| 9 | Water-dioxane (1:1) | Room | Room | 4 h | Weakly basic resin | 40.0% (*) |
| 10 | Water-dioxane (1:1) | 60° C. | 3000 Kpa (30 Kg/cm$^2$ gauge) | 4 h | Weakly basic resin | 73.5% (*) |

(*) Determined by gas-liquid chromatographic analysis

EXAMPLE 11

0.01 mole of butylene chlorohydrin was added to a suspension of 0.012 moles of tetramethylammonium bicarbonate in 25 cm$^3$ of acetonitrile, whereupon the procedure was as in Example 6.

EXAMPLE 15

Example 14 was repeated using water as the carbonation solvent for resin KASTEL A-300-OH and as the reaction solvent. The mixture was kept at 60° C. for 1.5 hours and under CO₂ pressure (2200 Kpa or 22 Kg/cm² gauge).

1.74 g of propylene carbonate, corresponding to a yield of 34%, were thus obtained (gas-liquid chromatographic analysis).

What is claimed is:

1. A process for the manufacture of alkylene carbonates, starting from a corresponding vicinal halohydrin of the formula:

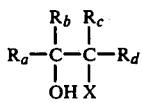

wherein $R_a$, $R_b$, $R_c$, and $R_d$, which can be the same or different, are hydrogen or alkyl, aryl, alkylaryl or arylalkyl radicals and X is a halogen, comprising reacting said halohydrin, in the presence of carbon dioxide and of an organic diluent, with the bicarbonate of a quaternary -onium compound, where "-onium" means ammonium, phosphomium, arsonium, or stibonium.

2. A process according to claim 1, wherein said organic solvent is acetonitrile.

3. A process according to claim 1, wherein the alkylene carbonate has from 2 to 4 atoms in the alkylene chain.

4. A process according to claim 1, wherein said halohydrin is a chlorohydrin, a bromohydrin or an iodohydrin.

5. A process according to claim 1, wherein said bicarbonate is the bicarbonate of a quaternary ammonium cation.

6. A process according to claim 5, wherein said bicarbonate is the bicarbonate of tetramethylammonium or of benzyltrimethylammonium.

7. A process according to claim 1, wherein said bicarbonate is the bicarbonate of a strongly basic anion exchange resin having quaternary ammonium end groups.

8. A process for synthesizing propylene carbonate, starting from propylene chlorohydrin, bromohydrin or iodohydrin, and in the presence of a diluent and of carbon dioxide, wherein said halohydrin is reacted with the bicarbonate of a quaternary -onium compound, using as said diluent an organic solvent.

9. A process according to claim 8, wherein said organic solvent is acetonitrile.

10. A process according to claim 8, wherein the synthesis temperature ranges from 0° to 100° C.

11. A process according to claim 8, wherein the synthesis temperature ranges from 20° C. to the boiling temperature of the organic solvent.

12. A process according to claim 9, wherein the carbon dioxide pressure is between 0 and 100 Kg/cm² gauge.

13. A process according to claim 12, wherein the carbon dioxide pressure is between 0 and 30 Kg/cm² gauge.

14. A process according to claim 8, wherein said bicarbonate is the bicarbonate of a quaternary ammonium cation.

15. A process according to claim 14, wherein said bicarbonate is trimethylammonium bicarbonate or benzyl-trimethylammonium bicarbonate.

16. A process improved according to claim 8, wherein said bicarbonate is the bicarbonate of a strongly basic anion exchange resin having quaternary ammonium end groups.

17. A process according to claim 16, wherein the synthesis is carried out in a bed of said resin suspended in the reaction liquid.

18. A process according to claim 16, wherein said resin is regenerated, after the synthesis.

19. A process according to claim 18, wherein the regeneration is effected by means of dilute aqueous NaOH or NH₄OH and successive carbonation with CO₂.

20. A process according to claim 16, wherein the synthesis is carried out in two or more reactors in parallel operating alternately.

21. A process according to claim 17, wherein the synthesis is carried out in two or more reactors in parallel operating alternately.

22. A process according to claim 18, wherein the synthesis is carried out in two or more reactors in parallel operating alternately.

* * * * *